United States Patent
De Guia et al.

(10) Patent No.: US 9,662,061 B2
(45) Date of Patent: *May 30, 2017

(54) ULTRAVIOLET CAMERA AND DISPLAY STATION FOR CAPTURING REFLECTED ULTRAVIOLET LIGHT

(71) Applicant: International Business Machines Corporation, Armonk, NY (US)

(72) Inventors: Brian C. De Guia, Tucson, AZ (US); Sandy Y. McDonald, San Jose, CA (US); Duy Q. Nguyen, Tucson, AZ (US); Esperanza D. Rodriguez, Tucson, AZ (US); Gary D. Williams, Driftwood, TX (US)

(73) Assignee: International Business Machines Corporation, Armonk, NY (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/106,949

(22) Filed: Dec. 16, 2013

(65) Prior Publication Data

US 2015/0164405 A1    Jun. 18, 2015

(51) Int. Cl.
*G06K 9/46*        (2006.01)
*A61B 5/00*        (2006.01)
(Continued)

(52) U.S. Cl.
CPC ............ *A61B 5/441* (2013.01); *A61B 5/0077* (2013.01); *G01J 1/0219* (2013.01); *G01J 1/429* (2013.01);
(Continued)

(58) Field of Classification Search
None
See application file for complete search history.

(56) References Cited

U.S. PATENT DOCUMENTS 4,704,535 A    11/1987    Leber et al.
4,985,632 A *   1/1991    Bianco et al. ............... 250/372
(Continued)

FOREIGN PATENT DOCUMENTS

JP       2008237243 A      10/2008
KR    1020120123628 A      11/2012

OTHER PUBLICATIONS

Computer Desktop Encyclopedia Terms, 'processor' retrieved from http://lookup.computerlanguage.com/host_app/search?cid=C999999&term=processor&lookup.x=O&lookup.y=O on Feb. 25, 2014.*

(Continued)

*Primary Examiner* — Vikkram Bali
*Assistant Examiner* — Tracy Mangialaschi
(74) *Attorney, Agent, or Firm* — Maeve Carpenter

(57) ABSTRACT

A tool for recommending proper sun block use. The tool receives, by one or more computer processors, a first image of a user captured by a camera, and a second image of a user captured by a camera, wherein the first image is an ultraviolet image, and the second image is a digital color image. The tool determines, by one or more computer processors, areas of ultraviolet radiation vulnerability for the user captured in the first and second image. The tool determines, by one or more computer processors, a level of ultraviolet radiation vulnerability for the determined areas. The tool determines, by one or more computer processors, a recommendation for proper sun block use based, at least in part, on the level of ultraviolet radiation vulnerability.

12 Claims, 3 Drawing Sheets

(51) Int. Cl.
  *G01J 1/42*     (2006.01)
  *G06K 9/62*     (2006.01)
  *G01J 1/02*     (2006.01)

(52) U.S. Cl.
  CPC .......... *G01J 1/4228* (2013.01); *G06K 9/4661* (2013.01); *G06K 9/6267* (2013.01); *G01J 2001/4266* (2013.01)

(56) References Cited

U.S. PATENT DOCUMENTS

| | | | |
|---|---|---|---|
| 5,148,023 | A | 9/1992 | Hayashi et al. |
| 5,363,854 | A | 11/1994 | Martens et al. |
| 5,365,068 | A * | 11/1994 | Dickerson ............ 250/372 |
| 7,349,857 | B2 | 3/2008 | Manzo |
| 7,477,767 | B2 | 1/2009 | Chhibber et al. |
| 8,260,010 | B2 | 9/2012 | Chhibber et al. |
| 2004/0125996 | A1* | 7/2004 | Eddowes ............ A61B 5/0059 382/128 |
| 2006/0092315 | A1* | 5/2006 | Payonk ............ A61B 5/0071 348/370 |
| 2010/0302247 | A1* | 12/2010 | Perez ............ G06K 9/00201 345/440 |
| 2011/0191272 | A1* | 8/2011 | McGuire ............ 706/11 |
| 2011/0304632 | A1* | 12/2011 | Evertt ............ G06F 3/011 345/474 |
| 2012/0250948 | A1 | 10/2012 | Rickman |
| 2013/0300850 | A1* | 11/2013 | Millikan ............ 348/77 |
| 2014/0085476 | A1* | 3/2014 | Toyofuku ............ B60Q 1/085 348/148 |

OTHER PUBLICATIONS

Rehg, James M., Maria Loughlin, and Keith Waters. "Vision for a smart kiosk." Computer Vision and Pattern Recognition, 1997. Proceedings., 1997 IEEE Computer Society Conference on. IEEE, 1997.*

Zhang, Zhengyou. "Microsoft kinect sensor and its effect." IEEE multimedia 19.2 (2012): 4-10.*

Singh, et al., "A Robust Skin Color Based Face Detection Algorithm", Tamkang Journal of Science and Engineering, vol. 6, No. 4, pp. 227-234 (2003), <http://www.csee.wvu.edu/~richas/papers/tkjse.pdf>.

Google, Patent US20040125996—Skin diagnostic imaging method and apparatus, Eddowes et al., U.S. Appl. No. 10/371,784, filed Feb. 21, 2003—Google Patents, <http://www.google.com/patents?id=RlyVAAAAEBAJ&zoom=4&dq=Skin%20Imaging%20UV%20Camera%20Highlight&pg=PA1#v=onepage&q=Skin%20Imaging%20UV%20Camera%20Highlight&f=false[9/6/2013]>.

REI, "Sunscreen: How to Choose", printed on [Sep. 6, 2013], <http://www.rei.com/learn/expert-advice/articles/sunscreen.html>.

SOLARTECH, Solarmeter® Excellence in Metrology, Radiometers—Scientific Grade, printed on [Sep. 6, 2013], <http://www.solarmeter.com/>.

UV HAWK™, "Owners Manual", provided by Inventor in Post Disclosure, Jan. 10, 2013, <http://www.smarthome.com/manuals/92912.pdf>.

Wikipedia, "Sunscreen—Wikipedia, the free encyclopedia", <http://en.wikipedia.org/wiki/Sunscreen#Sun_protection_factor_.28SPF.29[9/6/2013]>.

U.S. Appl. No. 14/478,104, filed Sep. 5, 2014.

* cited by examiner

ULTRAVIOLET CAMERA AND DISPLAY STATION FOR CAPTURING REFLECTED ULTRAVIOLET LIGHT

FIELD OF THE INVENTION

The present invention relates generally to healthcare, and more particularly to capturing ultraviolet light reflected away from the skin to determine vulnerability to ultraviolet light.

BACKGROUND OF THE INVENTION

The effects of the sun are an ongoing concern for many people who spend their days outdoors. Ultraviolet (UV) light is damaging to skin when the skin absorbs the UV rays. UV light cannot be seen by the human eye. Three types of UV light exist: UVA, UVB, and UVC. Typically, the ozone layer only allows UVA light to pass through, but as the ozone conditions deteriorate over time, it is thought that the amount of UVB passing through the ozone is increasing.

Exposure to UV light is increasing worldwide with the destruction of our protective ozone layer. It is estimated that 90% of UV radiation is of the common UVA type, which can pass through window glass. UVA type is thought to cause tanning and wrinkles in skin. UVB type exposure may depend on ozone quality, and is typically highest at midday. UVB type does not penetrate window glass, and is associated with sunburn. UVB type is considered to be more dangerous than the UVA type. UVC type may be mostly absorbed in the ozone, but is of high concern for the future as ozone conditions deteriorate. UV light has been linked to increases of several diseases such as skin cancer, immune suppression, and cataracts. In particular, skin cancer occurrences have been increasing steadily due in part to the effects of increasing UV radiation passing through our atmosphere.

Sun block is always recommended to prevent sunburn, skin cancer, and overall long term damage to the skin. Most sun blocks, after application, dry clear on the skin. Burns occur when sun block is applied too thinly, or possibly missed entirely. Sun block may lose its effectiveness when exposed to water for long periods of time, or it can rub off when people dry themselves with a towel. It is under these circumstances that it becomes unclear what parts of the body are protected by the sun block.

SUMMARY

Aspects of an embodiment of the present invention disclose a method, system, and computer program product for recommending proper sun block use. The method includes receiving, by one or more computer processors, a first image of a user captured by a camera, and a second image of a user captured by a camera, wherein the first image is an ultraviolet image, and the second image is a digital color image. The method includes determining, by one or more computer processors, areas of ultraviolet radiation vulnerability for the user captured in the first and second image. The method includes determining, by one or more computer processors, a level of ultraviolet radiation vulnerability for the determined areas. The method includes determining, by one or more computer processors, a recommendation for proper sun block use based, at least in part, on the level of ultraviolet radiation vulnerability.

BRIEF DESCRIPTIONS OF THE SEVERAL DRAWINGS

DETAILED DESCRIPTION

Figure 1:
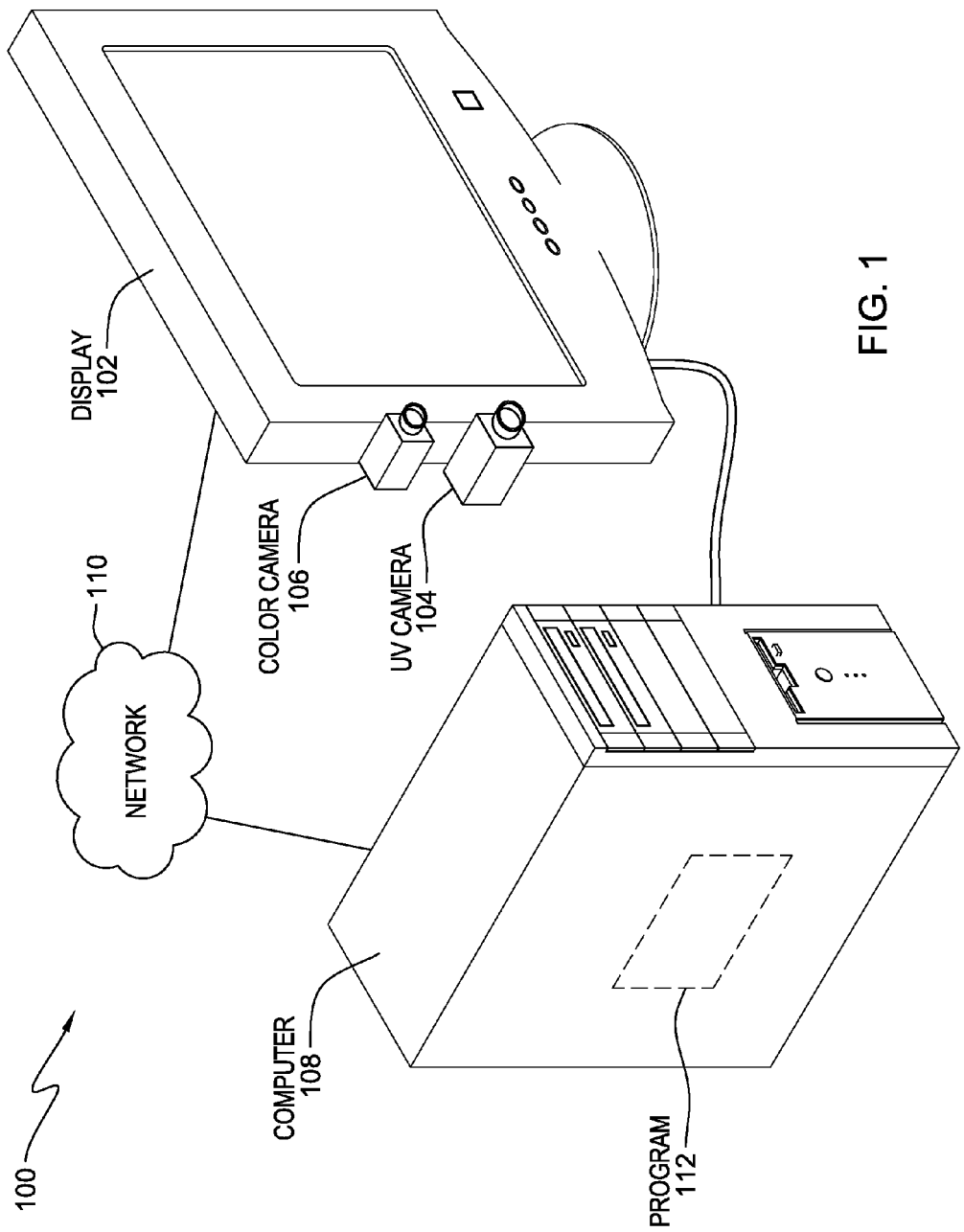
FIG. 1 is a functional block diagram illustrating a data processing environment, generally designated 100, in accordance with an embodiment of the present invention.

Sun safety is a matter of pubic health, and a reliable solution is needed to prevent sunburns, skin cancer, and long term skin damage. Embodiments of the present invention recognize that users need a solution that increases awareness of vulnerability to ultraviolet rays, and encourages the proper application of sun block.

Embodiments of the present invention provide the capability to increase awareness of vulnerability to ultraviolet rays and encourage the proper application of sun block by capturing images of ultraviolet rays reflected off of a user's skin, displaying areas at risk to sun damage, and suggesting the strength and placement of sun block to be applied.

As will be appreciated by one skilled in the art, aspects of the present invention may be embodied as a method, system, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer-readable media having computer readable program code/instructions embodied thereon.

Any combination of computer-readable media may be utilized. Computer-readable media may be a computer-readable signal medium or a computer-readable storage medium. A computer-readable storage medium may be, for example, but is not limited to, an electronic, magnetic, optical, electromagnetic, infrared, or semiconductor system, apparatus, or device, or any suitable combination of the foregoing. More specific examples (a non-exhaustive list) of a computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store, a program for use by, or in connection with, an instruction execution system, apparatus, or device.

A computer-readable signal medium may include a propagated data signal with computer-readable program code embodied therein, for example, in baseband or as part of a carrier wave. Such a propagated signal may take any of a variety of forms including, but not limited to, electromagnetic, optical, or any suitable combination thereof. A computer-readable signal medium may be any computer-readable medium that is not a computer-readable storage medium and that can communicate, propagate, or transport a program for use by, or in connection with, an instruction execution system, apparatus, or device.

Program code embodied on a computer-readable medium may be transmitted using any appropriate medium including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java®, Smalltalk, C++ or the like, and conventional procedural programming languages, such as the "C" programming language or similar programming languages. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions that execute via the processor of the computer or other programmable data processing apparatus, create means for implementing the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture, including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer-implemented process such that the instructions that execute on the computer or other programmable apparatus provide processes for implementing the functions/acts specified in the flowchart and/or block diagram block or blocks.

The present invention will now be described in detail with reference to Figures. FIG. 1 illustrates an exemplary data processing environment, generally designated 100, including display 102, UV camera 104, color camera 106, computer 108, and network 110, in accordance with an exemplary embodiment of the present invention.

In the exemplary embodiment, display 102 may be any suitable electronic visual display, including flat panel displays (FPDs), liquid crystal display televisions (LCDs), volumetric displays, plasma panels, electroluminescent panels, light-emitting diode displays (LED), and other volatile flat panel displays capable of presenting a plurality of information, such as images, text, video, streaming content, live feeds, animations and the like, for visual or tactile reception. In the exemplary embodiment, display 102 is an electronic visual display within a display station (not shown) configured to interact with a user. For example, display 102 may be an electronic visual display within a kiosk that users can approach and interact with. In another embodiment, display 102 may be an electronic visual display within a mobile device including smart phones, laptop computers, tablet computers, digital cameras, and personal digital assistants (PDAs) for presenting information for visual or tactile reception. For example, display 102 may be an electronic visual display within an iPhone® presenting information to a user for visual or tactile reception.

In an alternate embodiment, display 102 may be any wearable electronic visual display, including optical head-mounted displays (OHMDs), monocular and binocular helmet-mounted displays (HMDs), and heads-up displays (HUDs), capable of presenting a plurality of information, such as images, text, video, streaming content, live feeds, animations and the like, in an augmented reality (i.e., a computer generated image (CGI) superimposed on a real-world image) for visual or tactile reception. In the alternate embodiment, display 102 may be fully integrated with, partially integrated with, or separate from a wearable electronic device, including wearable electronic devices affixed to eyeglasses and sunglasses (e.g. Google Glass®), goggles (e.g., swim, SCUBA, glacier, etc.), helmets, wristwatches, clothing, and the like, capable of sending, receiving, and processing data. For example, display 102 may be an optical head-mounted display on the Google Glass® device presenting information to a user for visual or tactile reception.

In the exemplary embodiment, UV camera 104 may be any suitable digital camera capable of ultraviolet (UV) photography (i.e., cameras having lenses, sensors, and filters capable of responding to ultraviolet frequencies) including cameras capable of reflected UV photography, and UV induced fluorescence photography, such as digital single-lens reflex (DSLR) cameras. In the exemplary embodiment, UV camera 104 may be fully integrated with, partially integrated with, or separate from display 102. UV camera 104 provides the capability to capture images of reflected ultraviolet rays and present the images on an electronic visual display, such as display 102. In another embodiment, UV camera 104 may provide the capability to capture both images of reflected ultraviolet rays and digital color images. For example, UV camera 104 may be a DSLR camera capable of both capturing a digital color image, and then capturing an image of reflected ultraviolet rays. In the exemplary embodiment, UV camera 104 is oriented to point toward, and focus on, a user standing in front of display 102.

In the exemplary embodiment, color camera 106 may be any suitable color camera capable of digital photography (i.e., cameras utilizing electronic photo detectors to capture images focused by the lens and store the image as a digitized computer file ready for digital processing, viewing, or transmitting) including digital single-lens reflex (DSLR) cameras, smart phones with integrated digital cameras, compact digital cameras, and digital, mirrorless interchangeable-lens cameras. In the exemplary embodiment, color camera 106 may be fully integrated with, partially integrated with, or separate from display 102. Color camera 106 provides the capability to capture digital color images and present the images on an electronic visual display, such as display 102. In the exemplary embodiment, color camera 106 is oriented to point toward, and focus on, a user standing in front of display 102.

In the exemplary embodiment, computer 108 may be, for example, a server computer system such as a management server, web server, or any other electronic device or computing system capable of sending, receiving, and processing data. Computer 108 can be preloaded with a configuration of information gathered from research related to UV radiation vulnerability. For example, computer 108 may include a database (not shown) containing data on various levels of severity of UV radiation, and corresponding vulnerabilities to UV radiation exposure across differing skin tones, body parts, geographic locations and times of day, UV indices, and weather conditions. In another embodiment, computer 108 may retrieve information gathered from research related to UV radiation vulnerability via network 108. Computer 108 includes program 112 for gathering data related to UV radiation vulnerability, determining at-risk areas where high levels of UV radiation is apparent, and providing recommendations related to proper sun block use. Computer 108 may be fully integrated with, partially integrated with, or separate from display 102, UV camera 104, and color camera 106.

In the exemplary embodiment, program 112 receives a plurality of data points from one or more inputs (not shown), including UV index meters, temperature sensors, clocks, and global positioning systems (GPSs), defining current environmental conditions where display 102 is located. For example, program 112 may receive a local UV index factor from a UV index meter integrated with display 102. In another embodiment, program 112 may receive one or more of the aforementioned data points via network 110. For example, program 112 may receive a current local temperature and weekend weather forecast for Montauk, N.Y. from a weather website accessed via network 110. Program 112 receives images captured by UV camera 104 and color camera 106. Program 112 gathers relevant data from the images captured by UV camera 104 and color camera 106, and utilizing imaging software, determines levels of UV reflection and absorption from the images captured by UV camera 104 and color camera 106. Program 112 analyzes relevant environmental data points in conjunction with data gathered from the images captured by UV camera 104 and color camera 106 to determine recommendations regarding when and where to apply sun block.

In the exemplary embodiment, network 110 is the Internet representing a worldwide collection of networks and gateways that use TCP/IP protocols to communicate with one another. Network 110 may also be implemented as a number of different types of networks, such as an intranet, a local area network (LAN), or a wide area network (WAN). FIG. 1 is intended as an example, and not as an architectural limitation, for the different embodiments.

Figure 2:
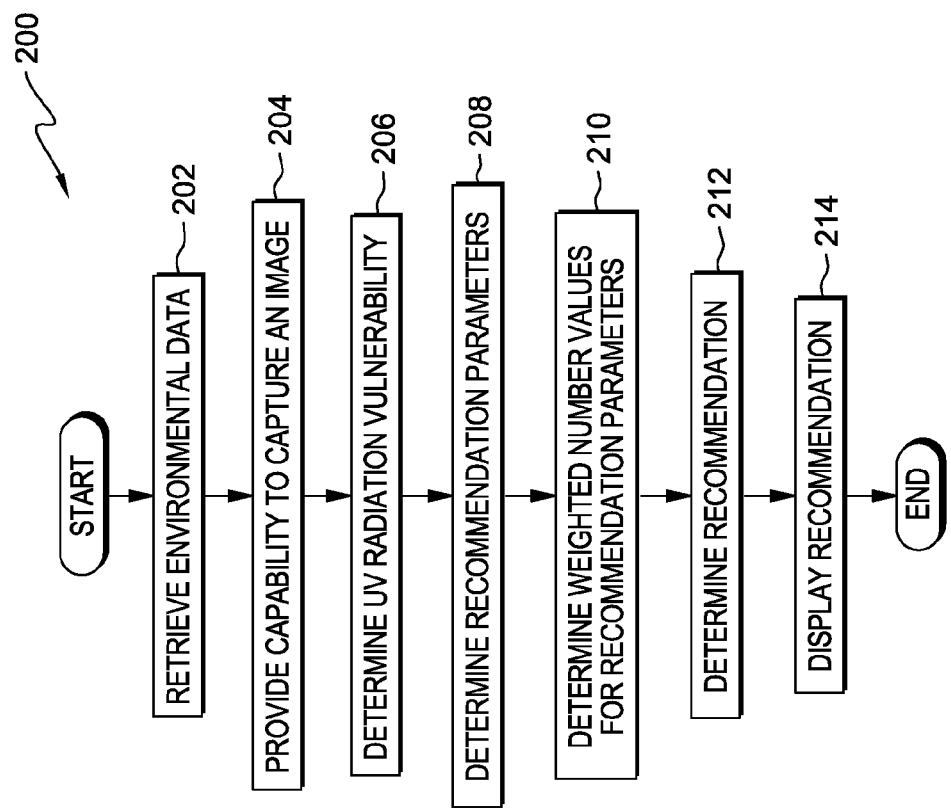
FIG. 2 is a flowchart of an exemplary process flow, generally designated 200, for determining areas on skin of a user that are vulnerable to UV radiation, and providing recommendations related to proper sun block use, in accordance with an embodiment of the present invention.

FIG. 2 is a flowchart depicting operational steps of program 112 for determining areas on skin of a user that are vulnerable to UV radiation, and providing recommendations related to proper sun block use, in accordance with an exemplary embodiment of the present invention.

Program 112 retrieves environmental data (step 202). In the exemplary embodiment, program 112 retrieves environmental data, such as UV index, time of day, geographical location, and weather conditions, through a plurality of input devices including UV meters, thermometers, GPSs, and connection to the Internet via network 110. For example, program 112 may retrieve the current UV index for Montauk, N.Y. at 12:00 PM EST by accessing a UV meter integrated into display 102 to obtain a current UV index, an internal clock to obtain the time of day, and a GPS to obtain a current location (e.g., for use with mobile device applications). Program 112 retrieves environmental data continuously, and may present one or more data points (i.e., time of day, weather conditions, etc.) on display 102 for visual reception by a user.

Program 112 provides the capability to capture an image of a user (step 204). In the exemplary embodiment, program 112 provides the capability to capture an image of a user that, for example, is positioned in front of display 102, and in the focus area of UV camera 104 and color camera 106. Program 112 utilizes motion and shape detection technology, such as in Kinect™ or Playstation Eye™ systems, integrated within color camera 106 to detect when a user is positioned in front of display 102, and outline the area of interest (i.e., map the contours of the body of a user three dimensionally). In response to program 112 detecting that a user is positioned in the focus area of UV camera 104 and color camera 106, program 112 provides the capability to capture the image of the user with UV camera 104 and color camera 106. For example, a user approaches a kiosk housing display 102, and stands in front of display 102 in the focus area of UV camera 104 and color camera 106. Program 112 utilizes motion and shape detection to detect that a user is positioned in front of display 102 and maps the contours of the body of the user. While program 112 outlines the area of interest, the user sees a mirror image of their body in real time on display 102 (i.e., the image being captured by color camera 106 is presented in real time on display 102). Once the area of interest is successfully defined, color camera 106 captures a color image from, and UV camera 104 captures a UV image. In the exemplary embodiment, program 112 continuously detects and provides the capability to capture images of a user for as long as the user is positioned in front of display 102 in the focus area of UV camera 104 and color camera 106. For example, when a user raises their arms, turns around, jumps, etc., program 112 detects and provides the capability to capture all these images in real time, and displays them to the user on display 102 as a live stream.

In response to receiving an image of a user, program 112 determines areas of UV radiation vulnerability (step 206). In the exemplary embodiment, program 112 determines UV radiation vulnerability by overlaying the image captured by UV camera 104 with the image captured by color camera 106. Program 112 crops the two overlaid images so that color image (i.e., the outline of the body of the user) is now superimposed with the UV images (i.e., the bright spots and dark spots). Program 112 determines areas of UV radiation vulnerability by matching various parts of the body captured in the color image with the corresponding light and dark spots captured in the UV images. In the color image, certain parts of the body, such as shoulders, face, chest, and back, are more susceptible to sunburn and UV radiation exposure than other parts of the body, such as inner legs and feet. In the UV image, bright spots indicate well protected areas, as the bright spots are created by UV rays being reflected off the body, and dark spots indicate poorly protected areas, as the dark spots are created by UV rays being absorbed into the body. For example, an image showing a user's shoulders with very dark spots indicates an area of high UV radiation vulnerability, whereas an image showing a user's feet with very bright spots indicates an area of low UV radiation vulnerability.

Program 112 determines a recommendation parameter (step 208). In the exemplary embodiment, program 112 determines one or more recommendation parameters, such as UV index, time of day, geographic location, skin tone, body part, weather conditions, and UV imaging spots (i.e., bright spots and dark spots present on the UV image), for use in determining a recommendation related to proper sun block use. Program 112 may be preloaded with a configuration of parameters for use in determining a recommendation related to proper sun block use. For example, program 112 may access a clock integrated within display 102 to determine the time of day recommendation parameter to be 12:00 PM, access a UV meter integrated within display 102 to determine the UV index recommendation parameter at level 3 (e.g., level 3 on a 0-11+scale), and access the image captured by color camera 106 to determine the skin tone recommendation parameter as fair skinned and the body part recommendation parameter as shoulders.

In response to determining a recommendation parameter, program 112 determines a weighted number value for the recommendation parameter (step 210). In the exemplary embodiment, program 112 determines a weighted number value for a recommendation parameter representing the impact the parameter has on the overall UV radiation vulnerability for a user. The weighted number value may fall within a weighted number range from very high UV radiation vulnerability (e.g., 4) to very low UV radiation vulnerability (e.g., −4). Program 112 determines a weighted number value for a recommendation parameter by accessing a database containing information from research related to UV radiation and, based on that information, assigns a weighted number value to the recommendation parameter based on the impact the recommendation parameter has on overall UV radiation vulnerability. For example, program 112 may assign a weighted number value of 4 (indicating very high UV radiation vulnerability) to the body part shoulders, as research supports the proposition that shoulders are highly vulnerable to UV radiation. Program 112 may assign a weighted number value of −3 (indicating a low UV radiation vulnerability) to a skin tone determined to be very dark, as research supports the proposition that darker skin tones are less vulnerable to UV radiation than fair skin tones. In another embodiment, program 112 may determine a weighted number value for a recommendation parameter by accessing information from research related to UV radiation via network 110 and, based on that information, assign a weighted number value to the recommendation parameter based on the impact the recommendation parameter has on overall UV radiation vulnerability.

In response to determining a weighted number value for a recommendation parameter, program 112 determines a recommendation on proper sun block use (step 212). In the exemplary embodiment, program 112 determines a recommendation by utilizing an algorithm that adds the weighted number values for each recommendation parameter to be considered in the recommendation, and determines where the sum of those weighted number values falls on a sun block use chart. For example, a sun block use chart may span a range of 0 (indicating a recommendation of no sun block is proper) to 16 (indicating a recommendation of sun protection factor (SPF) 60 or higher is proper). For example, the following parameters are to be considered in a recommendation on proper sun block use: UV index (U), with a weighted number of 3, time of day (T), with a weighted number of 2, geographic location (G), with a weighted number of 2, skin tone (S), with a weighted number of −2, and body part (B), with a weighted number of 4. Program 112 may use a formula, such as U+T+G+S+B, to determine an overall weighted number value. In the example above, the overall weighted number value may be expressed as 3+2+2+(−2)+4=9. Program 112 determines where the overall weighted number value falls within the range on the sun block use chart. For example, the overall weighted number value 9 may fall within the 9-12 range of the sun block use chart, indicating a recommendation of SPF 45 is proper. In the exemplary embodiment, program 112 may be configured to determine one or more recommendations for a user. For example, program 112 may be configured to determine a recommendation for any parts of the body on the overlaid image referenced above not reflecting UV radiation (i.e., determine a recommendation for all dark spots on the body of a user).

In response to determining a recommendation, program 112 displays the recommendation to the user (step 214). In the exemplary embodiment, program 112 displays the recommendation to the user on display 102 as a mirror-like image, in real time, visually highlighting parts of the user's body susceptible to UV radiation vulnerability accompanied by a text recommendation. For example, program 112 may visually highlight parts of the user's body susceptible to UV radiation vulnerability with colored rings around the at-risk body part (e.g., a yellow ring may indicate some risk to UV radiation, whereas a red ring may indicate high risk to UV radiation). Program 112 may display the recommendation in a text format on display 102, including the proper SPF to use and where to apply the SPF on the user's body. For example, the user may see text indicating that SPF 30 is the proper sun block to use, along with colored arrows directing the user to parts of their body requiring sun block.

Figure 3:
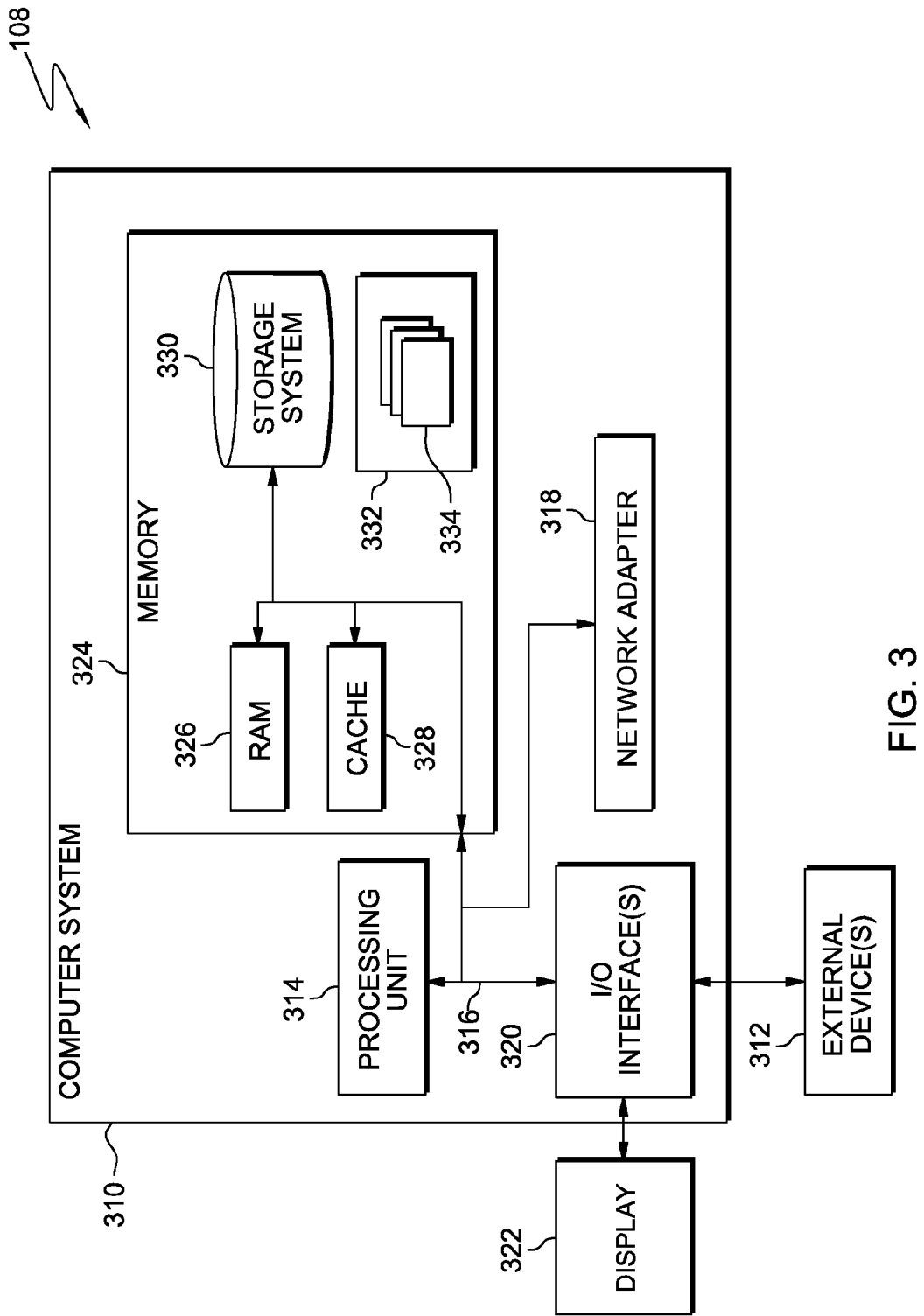
FIG. 3 is a block diagram depicting components of a data processing system (such as computer 108 of FIG. 1), in accordance with an embodiment of the present invention.

FIG. 3 depicts a block diagram of a component of data processing environment 100, such as computer 108, in accordance with an illustrative embodiment of the present invention. It should be appreciated that FIG. 3 provides only an illustration of one implementation and does not imply any limitations with regard to the environments in that different embodiments may be implemented. Many modifications to the depicted environment may be made.

In the illustrative embodiment, computer 108 in data processing system 100 is shown in the form of a general-purpose computing device. The components of computer system 310 may include, but are not limited to, one or more processors or processing units 314, a system memory 324, and a bus 316 that couples various system components including system memory 324 to processor 314.

Bus 316 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system 310 typically includes a variety of computer system readable media. Such media may be any available media that is accessible by computer system 310, and it includes both volatile and non-volatile media, removable and non-removable media.

System memory 324 can include computer system readable media in the form of volatile memory, such as random access memory (RAM) 326 and/or cache memory 328. Computer system 310 may further include other removable/non-removable, volatile/non-volatile computer system storage media. By way of example only, storage system 330 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each can be connected to bus 316 by one or more data media interfaces. As will be further depicted and described below, system memory 324 may include at least one computer program product having a set (e.g., at least one) of program modules that are configured to carry out the functions of embodiments of the invention.

Program/utility 332, having one or more sets of program modules 334, may be stored in memory 324 by way of example, and not limitation, as well as an operating system, one or more application programs, other program modules, and program data. Each of the operating systems, one or more application programs, other program modules, and program data, or some combination thereof, may include an implementation of a networking environment. Program modules 334 generally carry out the functions and/or methodologies of embodiments of the invention as described herein. Computer system 310 may also communicate with one or more external devices 312 such as a keyboard, a pointing device, a display 322, etc., or one or more devices that enable a user to interact with computer system 310 and any devices (e.g., network card, modem, etc.) that enable computer system 310 to communicate with one or more other computing devices. Such communication can occur via Input/Output (110) interfaces 320. Still yet, computer system 310 can communicate with one or more networks such as a local area network (LAN), a general wide area network (WAN), and/or a public network (e.g., the Internet) via network adapter 318. As depicted, network adapter 318 communicates with the other components of computer system 310 via bus 316. It should be understood that although not shown, other hardware and software components, such as microcode, device drivers, redundant processing units, external disk drive arrays, RAID systems, tape drives, and data archival storage systems may be used in conjunction with computer system 310.

The flowcharts and block diagrams in the figures illustrate the architecture, functionality, and operation of possible implementations of methods and systems according to various embodiments of the present invention. In this regard, each block in the flowcharts or block diagrams may represent a module, segment, or portion of code, which comprises one or more executable instructions for implementing the specified logical functions. It should be noted that, in some alternative implementations, the functions noted in the blocks may occur out of the order noted in the figures. For example, two blocks shown in succession may, in fact, be executed substantially concurrently, or the blocks may sometimes be executed in the reverse order, or the blocks may sometimes be executed any number of steps prior to, or subsequent to, their current place in the order, depending on the functionality involved.

The terminology used herein is for the purpose of describing particular embodiments only and is not intended to be limiting of the invention. It should be appreciated that any particular nomenclature herein is used merely for convenience and thus, the invention should not be limited to use solely in any specific function identified and/or implied by such nomenclature. Furthermore, as used herein, the singular forms of "a," "an," and "the" are intended to include the plural forms as well, unless the context clearly indicates otherwise.

The description of the present invention has been presented for purposes of illustration and description, but is not intended to be exhaustive or limited to the invention in the form disclosed. Many modifications and variations will be apparent to persons of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer program product embodied on one or more computer readable storage devices for recommending proper sun block use, the computer program product comprising:

program instructions stored on the one or more computer-readable storage devices, the program instructions executable by a processor, the program instructions comprising:

program instructions to map a plurality of contours of a body of a user, wherein mapping includes utilizing motion and shape detection technology integrated with a digital camera to detect when the user is positioned in front of a display and outline the plurality of contours of the body of the user;

program instructions to receive a first image of the user captured by a digital ultraviolet camera and a second image of the user captured by the digital camera, wherein the first image is an ultraviolet image, and the second image is a digital color image;

program instructions to determine areas of ultraviolet radiation vulnerability for the user captured in the first and second image;

program instructions to determine a level of ultraviolet radiation vulnerability for the determined areas;

program instructions to determine a recommendation for proper sun block use based, at least in part, on the level of ultraviolet radiation vulnerability, wherein determining the recommendation for proper sun block use includes determining a sun protection factor threshold from a sun block chart, wherein the sun block chart indicates the sun protection factor threshold for proper sun block use within a plurality of total weighted number value ranges, the total weighted number values based, at least in part, on a sum of weighted number values for each of a plurality of recommendation parameters, wherein the plurality of recommendation parameters includes a UV index value, a time of day value, a geographic location value, a skin tone value, and a body part value; and program instructions to present the recommendation for proper sun block use as a real time mirror image on the display, wherein the recommendation includes highlighting one or more parts of the user's body susceptible to ultraviolet radiation vulnerability with one or more colored rings around the one or more parts, a text recommendation indicating a sun protection factor to use, and one or more colored arrows directing the user to the one or more parts to apply the sun protection factor, wherein the one or more parts of the user's body susceptible to ultraviolet radiation vulnerability include parts of the body captured in the digital color image overlaid with one or more corresponding light and dark spots captured in the ultraviolet image.

2. The computer program product of claim 1 further comprises program instructions to retrieve environmental data related to ultraviolet radiation including one or more of:
an ultraviolet index;
a geographic location;
a time of day; and
a weather condition.

3. The computer program product of claim 1, wherein the program instructions to determine areas of ultraviolet radiation vulnerability, further comprise program instructions to overlay the first image and the second image to create a third image indicating areas on skin of the user where ultraviolet radiation absorption is present.

4. The computer program product of claim 1, wherein the program instructions to determine the recommendation for proper sun block use further comprise:
program instructions to determine a plurality of recommendation parameters, the plurality of recommendation parameters including one or more of, a skin tone, an ultraviolet index, a time of day, a geographic location, a specific body part, a weather condition, and a level of ultraviolet radiation; and
program instructions to determine, for each recommendation parameter, a weighted number value, wherein the weighted number value for each recommendation parameter is weighted proportionally to reflect the impact on ultraviolet radiation vulnerability from the recommendation parameter.

5. The computer program product of claim 1 further comprises program instructions to display the recommendation for proper sun block use, wherein the recommendation includes one or more of:
an area on the body to apply sun block;
a sun protection factor for sun block to apply;
a time of day;
an ultraviolet index; and
a weather condition.

6. The computer program product of claim 1, wherein the display is an electronic visual display within a kiosk display station for interacting with the user and presenting a plurality of images, text, video, streaming content, and live feeds for visual reception.

7. The computer program product of claim 1, further comprises:
program instructions to utilize motion detection to detect when the user is positioned in front of the display; and
program instructions to utilize shape detection to map a plurality of contours of the user's body.

8. A computer system for recommending proper sun block use, the system comprising:
one or more computer processors;
one or more computer-readable storage devices;
program instructions stored on at least one of the one or more computer-readable storage devices for execution by at least one of the one or more computer processors, the program instructions comprising:
program instructions to map a plurality of contours of a body of a user, wherein mapping includes utilizing motion and shape detection technology integrated with a digital camera to detect when the user is positioned in front of a display and outline the plurality of contours of the body of the user;
program instructions to receive a first image of the user captured by a digital ultraviolet camera and a second image of the user captured by the digital camera, wherein the first image is an ultraviolet image, and the second image is a digital color image;
program instructions to determine areas of ultraviolet radiation vulnerability for the user captured in the first and second image;
program instructions to determine a level of ultraviolet radiation vulnerability for the determined areas;
program instructions to determine a recommendation for proper sun block use based, at least in part, on the level of ultraviolet radiation vulnerability, wherein determining the recommendation for proper sun block use includes determining a sun protection factor threshold from a sun block chart, wherein the sun block chart indicates the sun protection factor threshold for proper sun block use within a plurality of total weighted number value ranges, the total weighted number values based, at least in part, on a sum of weighted number values for each of a plurality of recommendation parameters, wherein the plurality of recommendation parameters includes a UV index value, a time of day value, a geographic location value, a skin tone value, and a body part value; and
program instructions to present the recommendation for proper sun block use as a real time mirror image on the display, wherein the recommendation includes highlighting one or more parts of the user's body susceptible to ultraviolet radiation vulnerability with one or more colored rings around the one or more parts, a text recommendation indicating a sun protection factor to use, and one or more colored arrows directing the user to the one or more parts to apply the sun protection factor, wherein the one or more parts of the user's body susceptible to ultraviolet radiation vulnerability include parts of the body captured in the digital color image overlaid with one or more corresponding light and dark spots captured in the ultraviolet image.

9. The computer system of claim 8, wherein the program instructions to determine the recommendation for proper sun block use further comprise:
program instructions to determine a plurality of recommendation parameters, the plurality of recommendation parameters including one or more of, a skin tone, an ultraviolet index, a time of day, a geographic location, a specific body part, a weather condition, and a level of ultraviolet radiation; and
program instructions to determine, for each recommendation parameter, a weighted number value, wherein the weighted number value for each recommendation parameter is weighted proportionally to reflect the impact on ultraviolet radiation vulnerability from the recommendation parameter.

10. The computer system of claim 8 further comprises program instructions to display the recommendation for proper sun block use, wherein the recommendation includes one or more of:
an area on the body to apply sun block;
a sun protection factor for sun block to apply;
a time of day;
an ultraviolet index; and
a weather condition.

11. The computer system of claim 8, wherein the display is an electronic visual display within a kiosk display station for interacting with the user and presenting a plurality of images, text, video, streaming content, and live feeds for visual reception.

12. The computer system of claim 8, further comprises:
program instructions to utilize motion detection to detect when the user is positioned in front of the display; and
program instructions to utilize shape detection to map a plurality of contours of the user's body.

\* \* \* \* \*